United States Patent
Sunjic et al.

[11] Patent Number: 5,733,755
[45] Date of Patent: Mar. 31, 1998

[54] METHOD FOR THE ENANTIOSELECTIVE SYNTHESIS OF CHIRAL DERIVATIVES OF S-3-(4'-TERT-BUTYL)-PHENYL-2-METHYL PROPYLAMINE, SYSTEMIC FUNGICIDES

[75] Inventors: Vitomir Sunjic; Maja Majeric; Zdenko Hamersak; Amir Avdagic, all of Zagreb, Croatia

[73] Assignee: Industrie Chimiche Capparo S.p.A., Milan, Italy

[21] Appl. No.: 746,026

[22] Filed: Nov. 5, 1996

[30] Foreign Application Priority Data

Nov. 24, 1995 [IT] Italy .................. MI95A2442

[51] Int. Cl.$^6$ .................. C12P 41/00; C12P 17/14; C12P 17/12; C12P 17/10
[52] U.S. Cl. .................. 435/120; 435/121; 435/122; 435/128; 435/280; 435/942
[58] Field of Search .................. 435/280, 128, 435/942, 122, 120, 121

[56] References Cited

PUBLICATIONS

APS ABS EP 645458 Sunjic et al (Mar. 29, 1995).
Derwent ABS WPIL 91-305256/42 Isenring et al EP-452267 (Oct. 16, 1991).
Derwent ABS WPI 80-64582C/37 Himmele et al EP-14999 (Sep. 3, 1980).

*Primary Examiner*—Herbert J. Lilling
*Attorney, Agent, or Firm*—R. Neil Sudol; Henry D. Coleman

[57] ABSTRACT

A method for manufacturing S-3-(4'-tert-butyl)-phenyl-2-methyl propylamines having the structure I

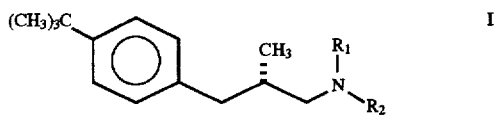

where $NR_1R_2$ is a dialkylamine group, pyrrolidine, piperidine, or cis-3,5-dimethyl morpholine, comprising a reduction of the compound having the structure II

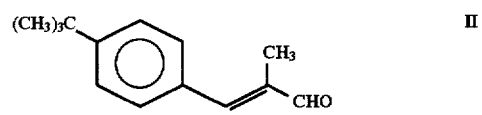

8 Claims, No Drawings

METHOD FOR THE ENANTIOSELECTIVE SYNTHESIS OF CHIRAL DERIVATIVES OF S-3-(4'-TERT-BUTYL)-PHENYL-2-METHYL PROPYLAMINE, SYSTEMIC FUNGICIDES

BACKGROUND OF THE INVENTION

1. Field of the Invention

The invention generally relates to the manufacture of chiral derivatives of S-3-(4'-tert-butyl)-phenyl-2-methyl propylamine with high optical and chemical purity. These derivatives are generally enantiomers that are biologically active with a fungicidal activity.

The most important parasites that cause foliar infections of plants are the powdery mold fungus and the rust fungus. It is estimated that more than six million hectares of cultivated land are damaged in Europe alone. The activity of conventional fungicides, for example dithiocarbamates, is substantially limited owing to the fact that they protect the surface only by direct contact with the spores of the fungi. These fungicides are directly exposed to the rain, to the air, to the light, and so forth, and cannot offer protection to many parts of the plant during the period of quick growth.

2. Description of the Prior Art

Systemic fungicides are instead expected to provide quick supply and distribution, through the roots and the leaves, regardless of the type of plant, in all the parts of the plant, and a wide-spectrum fungicidal activity. The discovery and development of this class of compounds have already been described (W. Himmele, E. H. Pommer, Angew. Chem. Int. Ed. Engl. 19 (1980) 184–189). More recently, attention has been devoted instead to an aspect of the compounds used in plant protection, that is to say, to the chirality of many active structures, and usually to great differences between the selective activity and toxicity of individual enantiomers (G. M. Ramos Tombo, D. Bellus, Angew. Chem. Int. Ed. Engl. 30 (1991) 1193–1215). Detailed structural and biological studies have revealed many implications of stereoisomerism in the biological activity of fungicides (A. J. Ariens, J. J. S. van Rensen, W. Welling (Eds.) Stereoselectivity of Pesticides, Elsevier, Amsterdam, 1988).

Racemic 1-[3-(4'-tert-butyl)-phenyl-2-methyl] propyl-cis-3,5-dimethyl morpholine, registered under the generic name of fenpropimorph, has a high fungicidal activity (German patent no. 2,656,747, granted to BASF AG; Chem. Abstr. 89 (1978) 109522k). It is used commercially as a racemic mixture, although past studies demonstrate that the S-enantiomer has a much higher fungicidal activity than the R-enantiomer (German patent 2,907,614, granted to BASF AG; Chem. Abstr. 94 (1981) 65703s). The first published preparation of S-(-)-fenpropimorph describes the separation of racemic fenpropimorph with camphosulfonic acid or with tartaric acid as chiral resolution agents (German patent 2,907,614, granted to BASF AG; Chem. Abstr. 94 (1981) 65703s). This method requires the manipulation of racemic material, and half of the final product must be discarded, since its recycling for racemization is not possible owing to the high stability of the chiral center on the tertiary carbon atom. The "wrong" enantiomer is an economic drawback and an ecological problem.

Accordingly, the importance of a stereoselective synthesis of S-(-)-fenpropimorph is evident. The Applicant has filed European patent application no. 93330389.8 (1993), which describes the production of this compound by virtue of a method which entails, in the fundamental stage, the kinetic resolution of 3-(4'-tert-butyl)-phenyl-2-methyl propionic acid. This is achieved by hydrolysis, catalyzed by Pseudomonas sp. lipase, of an ester of 3-(4'-tert-butyl)-phenyl-2-methyl propionic acid, followed by the acylation of 3,5-cis-dimethyl morpholine from the chloride of the S-(-)-form of the acid and by the reduction of the intermediate amide to S-(-)-fenpropimorph; A. Avdiagic et al., Biocatalysis, 9 (1994) 49–60. Although this method allows easy recycling of the R—0 enantiomer by basic racemization of the ester, the theoretical yield of the individual kinetic resolution stage cannot exceed 50% and this constitutes a technological drawback and particularly a limitation of productive capacity.

Racemic 1-[3-(4'-tert-butyl)-phenyl-2-methyl] propyl piperidine, registered under the generic name of fenpropydine, is another systemic fungicide, marketed as a racemic mixture (P. Ackermann, P. Margot, C. Klotsche, Fungicides, Agricultural, in Ullmann's Encyclopaedia of Industrial Chemistry, Vol A12, VCH, (1989), p. 86–116). It has been shown that its S— enantiomer offers greater activity with respect to the R— enantiomer or to the racemic mixture (Coster-Corio, M. F., Benveniste, P., Pestic. Sci. 22, (1988) 343). Its preparation by asymmetric hydrogenation with homogeneous chiral catalysts has recently been claimed (Eur. Pat. Appl. 91121704.0 (1991), granted to Ciba Geigy AG).

Detailed kinetic and structural studies performed by Fuganti et al. (C. Fuganti et al. J. Chem. Soc. Chem. Commun. (1975), 846) have indicated that 2-methyl cinnamaldehyde is reduced to 2-methyl-3-phenyl propanol by forming the saturated aldehyde. According to this mechanism, the unsaturated alcohol produced by the reduction of the aldehyde group in the first stage constitutes a final product, and has been either isolated as main product or slowly converted to the saturated alcohol.

SUMMARY OF THE INVENTION

An object of the present invention is therefore to exceed known processes and overcome their drawbacks with a new method for the production of S-3-(4'-tert-butyl)-phenyl-2-methyl manufacture having the structure I

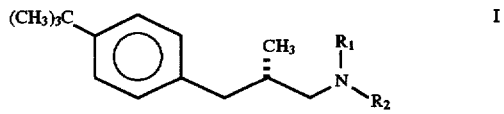

where $NR_1R_2$ is a dialkylamine group, pyrrolidine, piperidine, or cis-3,5-dimethyl morpholine, which comprises a reduction of the compound having the structure II

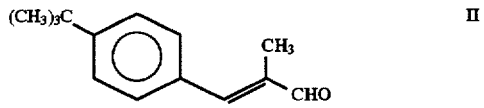

In fact it has surprisingly been discovered that the reactivity of 2-methyl cinnamaldehyde is completely reversed due to the presence, in position 4', of the tert-butyl substituent group. Without wanting to be bound by any theory, and with the sole purpose of proposing one of the possible explanations, it is possible that "masking" of the aromatic ring by the tert-butyl group in the para position causes the 2-methylcinnamaldehyde to become a particularly suitable substrate for yeast enoate-reductase. Moreover, the same group selectively increases the reactivity of the unsaturated α—β C═C bond, so much that its reduction becomes the main reaction path, whereas the forming of the unsaturated alcohol as final product is extensively suppressed. This unexpected and complete change in the reactivity of the p-tert-butyl-2-methyl derivative of cinnamaldehyde might be explained by the strong stabilization of the carbocationic species (transition state) that undergoes the nucleophilic attack of the electron or of the hydride ion.

The method preferably includes the use of reducing organisms, preferably of the standard species of Saccharomyces cerevisiae, preferably with aeration, so as to provide the necessary amount of oxygen.

The addition of specific nutrients, such as D-glucose, is preferably provided for.

4'-tert-butyl-2-methyl cinnamic aldehyde can be reduced effectively to S-3-(4'-tert-butyl)-phenyl-2-propanol.

This chiral synthon can be chlorinated without racemization, by using appropriate chlorination agents, such as thionyl chloride, phosphorus oxychloride, or bis-trichloromethyl carbonate (triphosgene, BTC)/PPh$_3$. By alkylation of the appropriate secondary amine in the last stage, such as piperidine and cis-3,5-dimethyl morpholine, the compounds mentioned in the title are obtained in an optically pure form. This final stage can conveniently be performed in polar aprotic solvents, such as dimethylformamide or tetrahydrofuran, or in an excess of the same secondary amine as solvent.

As a whole, the inventive combination outlined in Diagram 1 is a technologically effective and economically convenient method for the enantioselective production of S enantiomers of systemic fungicides derived from S-3-(4'-tert-butyl)-phenyl-2-methyl propylamine. The most interesting products from the commercial point of view are fenpropidin and fenpropimorph, which are commercially available as racemic mixtures with systemic fungicidal activity.

Diagram 1

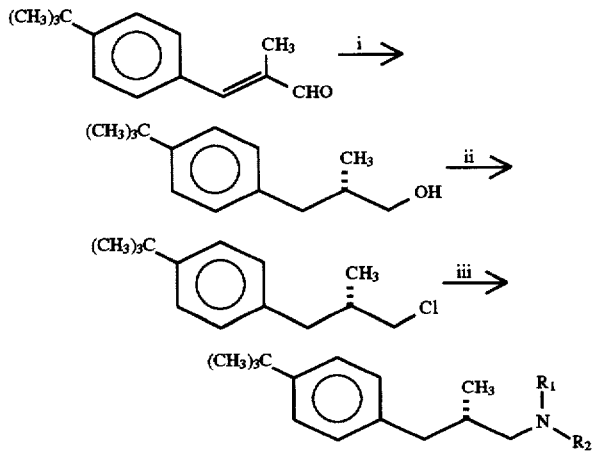

i. Saccharomyces Cerevisiae, D-glucose, ambient temperature, aeration.
ii. Triphosgene/PPh$_3$
iii. HNR$_1$R$_2$/(polar solvent)[delta].

DETAILED DESCRIPTION OF THE INVENTION

The following examples have the purpose of exemplifying the invention without limiting it in any way.

Example 1

S-(−)-2-methyl-3-(4'-tert-butyl)-phenyl propanol-1

D-glucose (10 g) was added to 200 ml of distilled water, followed by 20 g of fresh brewer's yeast (approximately 30% of dry substance ) and 0.5 g of 2-methyl-(4'-tert-butyl) cinnamaldehyde, dissolved in 5 ml of ethanol. The reaction mixture was aerated with a stream of oxygen, at ambient temperature and with strong agitation. The development of the reaction was followed by GLC, using an HP 17 column at 180° C., injector and detector temperature 300° C. nitrogen pressure 10 kPa. The samples (2 ml) were taken at uniform time intervals, extracted with ethyl acetate ( 4 ml ), dehydrated, and dried. The residual oil was dissolved in n-hexane (1 ml), filtered through a Millipore filter, evaporated to approximately 0.2 ml, and 3 µl were injected. After approximately 20 hours, that is to say, after total conversion, the reaction mixture was extracted with 2×400 ml of ethyl acetate. The organic phase was dried on Na$_2$SO$_4$, evaporated to dryness, and the crude product was purified by silica gel chromatography, using methylene chloride-cyclohexane (6:4) as eluent. The pure product (82%) has an $[\alpha]_D \pm 6.2$ (c 2.5 in CHCl$_3$). Its optical purity (enantiomer excess) was 99%, determined on an HPLC Chiralcel OD chiral column, using n-hexane-isopropanol as eluent.

Example 2

S-(−)-2-methyl-3-(4'-tert-butyl)-phenyl propanol-1

2-methyl-(4'-tert-butyl) cinnamaldehyde was reduced as described in Example 1, except for the fact that the D-glucose (30g) was added in two portions: 20 g at the beginning of the reaction and 10 g after 15 hours. The crude product was extracted with ethyl acetate in a soxhlet type extractor and isolated by solvent evaporation and distillation. 86% of pure product was obtained, with a boiling point of 85°–87° C./0.07 mmHg.

Example 3

S-(+)-1-chloro-2-methyl-3-(4'-tert-butyl)-phenyl propane

Triphosgene (0.12 mg, 0.4 mmol) was added to the solution of triphenyl phosphine (0.27 g, 1.0 mmol) in methylene chloride (4 ml), cooled to 0° C. When the development of CO$_2$ ended, the solution was still kept under agitation for 15 minutes, evaporated to dryness, and S-(−)-2-methyl-3-(4'-tert-butyl)-phenyl propanol-1 (0.14 g, 0.7 mmol) in methylene chloride (5 ml) was added to the crystalline residue. The resulting solution was heated to 45° C. for 2.5 hours, and the development of the reaction was monitored by TLC, using methylene chloride/cyclohexane ( 8:2 ) as eluent. A pure product (0.146 g, 93.1% ) was obtained by flash chromatography on silica gel, using methylene chloride/cyclohexane ( 6:4) as eluent, and by subsequent distillation; b.p. 87°–89° C./0.3 mm Hg, $[\alpha]_D$ +20.3 (c 3, in CHCl$_3$). Quantitative analysis for C$_{14}$H$_{21}$Cl (224.77): calculated: C 74.81, H 9.42; found: C 74.78, H 9.48%.

IR (KBr) 2960, 2875, 1460, 1370, 1270, 1110 cm$^{-1}$.

$^1$H-NMR (CDCl$_3$): 1.03 (d, J 6.7 Hz, 3H), 1.31 (s, 9H), 2.06–2.16 (m, 2H), 2.51 (dd, J$_1$ 13.5 Hz, J$_2$ 7.1, 1H), 2.72 (dd, J$_1$ 13.6 Hz, J$_2$ 7.2, 1H), 3.37–3.49 (m, 1H) 7.10 (d, J 8.2 Hz, 2H), 7.30 (d, J 8.2 Hz, 2H).

$^{13}$C-NMR (CDCl$_3$): 17.52, 31.13, 37.16, 39.32, 50.24, 125.14, 128.72, 136.60, 148.89.

Example 4

S-(+)-1-(1'-piperidine)-2-methyl-3-(4'tert-butyl)-phenyl propane

A solution of S-(−)-1-chloro-2-methyl-3-(4'-tert-butyl)-phenyl propane (0.22 g, 1.0 mmol) in piperidine (2 ml) was heated under nitrogen to 100° C. for 13 hours. The development of the reaction was monitored by GLC on an HP-17 column, chamber temperature 120° C. injector and detector temperature 300° C., temperature gradient 10° C./min up to 240° C. The piperidine excess was evaporated with the addition of toluene (2×5 ml), and the residual oil was dissolved in ethyl acetate-cyclohexane (3 ml, 3:1 ) HCl gas was introduced into the solution, and cooling to complete precipitation was performed. The pure free base was obtained by neutralization of the hydrochloride with aqueous bicarbonate, extraction, and evaporation (0.21 g, 76.7%), $[\alpha]_D$ +6.0 (c 3, in EtOH), b.p. 121°–124° C./0.2 mm Hg.

IR (KBr): 2965, 2800, 2760, 1515, 1460, 1370, 1270.

$^1$H-NMR (CDCl$_3$): 0.833 (d, J 6.4 Hz, 3 H), 1.31 (s, 9H), 1.35–1.47 (m, 2H), 1.52–1.60 (m, 4H), 1.92–1.98 (m, 1H), 2.04–2.17 (m, 2H), 2.23 (dd, J$_1$ 13.5 Hz, J$_2$ 8.4 Hz, 1H), 2.29–2.33 (m, 4H), 2.79 (dd, J$_1$ 13.6 Hz, J$_2$ 8.8 Hz, 1H), 7.10 (d, J 8.2 Hz, 2H), 7.28 (d, J 8.1 Hz, 2H).

Optical purity was measured on a Chiral AGP column, using 0.05 M NaH$_2$PO$_4$, pH 4.6, with 0.3% of isopropanol as eluent.

$^{13}$C-NMR (CDCl$_3$): 17.93, 24.46, 25.92, 31.24, 32.21, 34.11, 40.66, 54.84, 65.79, 124.84, 128.86, 138.26, 148.24.

Example 5

S-(−)-1-(1'-piperidine)-2-methyl-3-(4'-tert-butyl)-phenyl propane

Starting from S-(−)-1-chloro-2-methyl-3-(4'-tert-butyl)-phenyl propane (1.1 g, 5.0 mmol) and piperidine (2 ml), the reaction was carried out in dimethylacetamide (DMA, 8 ml), heating the reaction solution to reflux for 8 hours. The crude product was isolated by evaporation and purified as described in Example 4. The pure compound was obtained with an 89% yield, with an optical purity (enantiomer excess) of 94.8%.

Example 6

S-(−)-1-(3',5'-cis-dimethyl morpholine)-2-methyl-3-(4'-tert-butyl)-phenyl propane A solution of S-(+)-1-chloro-2-methyl-3-(4'-tert-butyl)-phenyl propane (0.18 g, 0.8 mmol) in cis-3,5-dimethyl morpholine (1 ml) was heated under nitrogen to 100° C. for 14 hours. The development of the reaction was monitored by GLC on an HP-17 column, chamber temperature 120° C., injector and detector temperature 300° C. The excess reagent was removed by evaporation with toluene (2×3 ml) and the residual oil was dissolved in ethyl acetate-cyclohexane (3 ml, 1:1); then HCl was introduced into the solution. Colorless hydrochloride crystals precipitated by cooling. These crystals were collected on the filter, washed with ethyl acetate (2 ml), and dried. Dissolution of the hydrochloride in dichloromethane and washing of the organic solution with aqueous bicarbonate (2×5 ml) and water provided the free base (0.19 g, 75.3%, 97.5% GLC titer), b.p. 126°–130° C./02 mm Hg, $[\alpha]_D$ −3.87 (c 1.1, in CHCl$_3$). C$_{20}$H$_{33}$NO (303.49); calculated: C 79.15, H 10.96%. Found: C 79.33, H 10.72%.

IR (KBr): 2960, 2850, 1510, 1370, 1320, 1140, 960 cm$^{-1}$.

$^1$H-NMR (CDCl$_3$): 0.85 (d, J 6.4 Hz, 3H), 1.15 (d, J 6.4 Hz, 6H), 1.31 (s, 9H), 1.50–2.75 (m, 9H), 3.57–3.78 (m, 2H), 7.06 (d, J 8.2 Hz, 2H), 7.29 (d, J 8.4 Hz, 2H).

$^{13}$C-NMR (CDCl$_3$): 19.02, 31.34, 31.79, 34.13, 40.57, 59.70, 59.97, 64.83, 71.50, 124.76, 126.23, 137.76, 148.15.

Example 7

S-(−)-1-(3', 5'-cis-dimethyl morpholine)-2-methyl-3-(4'-tert- butyl)-phenyl propane A solution of S-(+)-1-chloro-2-methyl-3-(4'-tert-butyl)-phenyl propane (0.36 g, 1.6 mmol) and of cis-3,5-dimethyl morpholine (1.5 ml) in toluene (10 ml) was heated under nitrogen to 100° C. for 24 hours. The crude product was separated by evaporation of the solvent and of the excess morpholine, as described in Example 5. Distillation provided the pure product with a yield of 82% and a chromatographic titer of 98.2%.

We claim:

1. A method for manufacturing S-3-(4'-tert-butyl)-phenyl-2-methyl propylamine having the structure I:

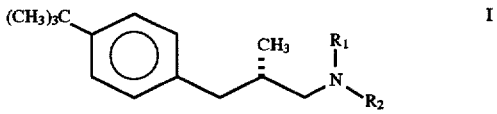

where NR$_1$NR$_2$ is a dialkylamine group, pyrrolidine, piperidine or cis-3,5-dimethyl morpholine comprising the steps of:

i) subjecting compound II

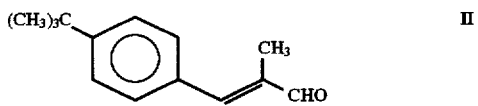

to fermentative reduction to obtain compound III;

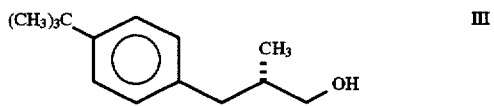

ii) chlorinating compound III to obtain a compound having structure IV;

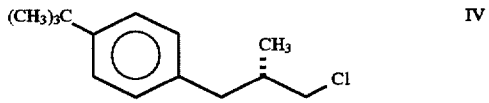

iii) reacting said compound of structure IV with a secondary amine having the formula HNR$_1$R$_2$ to obtain the compound of formula I.

2. The method according to claim 1 wherein said fermentative reduction occurs in the presence of *Saccharomyces cerevisiae*, nutrients and oxygen.

3. The method according to claim 2 wherein said nutrients include D-glucose and said oxygen is produced by aeration.

4. The method according to claim 1 wherein said chlorination step occurs in the presence of bistrichloromethyl carbonate/PPh$_3$, thionyl chloride or phosphorus oxychloride under conditions which avoid racemization.

5. The method according to claim 1 wherein HNR$_1$R$_2$ is a secondary amine.

6. The method according to claim 1 wherein HNR$_1$R$_2$ is selected from the group consisting of pyrrolidine, piperidine and cis-3,5-dimethyl morpholine.

7. The method according to claim 6 wherein said reaction iii) occurs in the presence of an aprotic solvent or an excess of said amine.

8. The method according to claim 7 wherein said polar aprotic solvent is selected from the group consisting of dimethylformamide and dimethylacetamide.

* * * * *

UNITED STATES PATENT AND TRADEMARK OFFICE
CERTIFICATE OF CORRECTION

PATENT NO. : 5,733,755
DATED : Mar. 31, 1998
INVENTOR(S) : Sunjic et al.

It is certified that error appears in the above-indentified patent and that said Letters Patent is hereby corrected as shown below:

ON THE TITLE PAGE:

Item [73], "Assignee", change "Capparo" to --Caffaro--.

Signed and Sealed this

Seventh Day of July, 1998

Attest:

BRUCE LEHMAN

*Attesting Officer*      *Commissioner of Patents and Trademarks*